US012788224B2

(12) United States Patent
Reinacher

(10) Patent No.: US 12,788,224 B2
(45) Date of Patent: Nov. 10, 2026

(54) ENDOSCOPE HAVING A RIGID OR FLEXIBLE SHAFT TUBE

(71) Applicant: KARL STORZ SE & CO. KG, Tuttlingen (DE)

(72) Inventor: Joachim Reinacher, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 119 days.

(21) Appl. No.: 18/826,695

(22) Filed: Sep. 6, 2024

(65) Prior Publication Data

US 2025/0072729 A1 Mar. 6, 2025

(30) Foreign Application Priority Data

Sep. 6, 2023 (DE) ........................ 10 2023 123953.8

(51) Int. Cl.
*A61B 1/00* (2006.01)
*A61B 1/05* (2006.01)

(52) U.S. Cl.
CPC .......... *A61B 1/00183* (2013.01); *A61B 1/051* (2013.01)

(58) Field of Classification Search
CPC . A61B 1/00183; A61B 1/051; A61B 1/00174; A61B 1/00177; A61B 1/00179; A61B 1/00181
See application file for complete search history.

(56) References Cited

U.S. PATENT DOCUMENTS 12,035,883 B2 7/2024 Schwarz
2007/0055103 A1* 3/2007 Hoefig ............... A61B 1/00179 600/137
2012/0123212 A1* 5/2012 Dahmen ............ G02B 23/2423 600/178
(Continued)

FOREIGN PATENT DOCUMENTS

DE 102005015522 A1 10/2006
DE 102020132776 A1 6/2022
(Continued)

OTHER PUBLICATIONS

Hoß, Theresa, Extended European Search Report, Jan. 24, 2025, pp. 1-8, European Patent Office, Munich, Germany.
(Continued)

*Primary Examiner* — Timothy J Neal
(74) *Attorney, Agent, or Firm* — Jason Worgull; David N. Villalpando; Jacqueline Cohen

(57) ABSTRACT

The disclosure relates to an endoscope having a rigid or flexible shaft tube, which comprises a rotary drum and is mounted at a distal end, preferably on a mounting fork, so as to be rotatable about at least one axis of rotation, wherein the rotary drum comprises a recess in which an associated imaging system is at least partially accommodated, which comprises at least one imaging optical unit and an image sensor, wherein the imaging system is conductively connected to the proximal region of the endoscope by a preferably flexible circuit board, and wherein the endoscope has at least one control means for moving the rotary drum, in particular for rotating it about the at least one rotational axis. According to the disclosure, the rotary drum is designed as a single piece, preferably monolithically, and has at least one preferably resilient control extension.

20 Claims, 2 Drawing Sheets

(56) References Cited

U.S. PATENT DOCUMENTS

| | | | |
|---|---|---|---|
| 2015/0359420 A1 | 12/2015 | Hatase et al. |
| 2022/0175219 A1 | 6/2022 | Schwarz |
| 2022/0175225 A1 | 6/2022 | Schwarz |
| 2022/0248946 A1 | 8/2022 | O'Callaghan et al. |

FOREIGN PATENT DOCUMENTS

| | | | |
|---|---|---|---|
| DE | 102020132778 | A1 | 6/2022 |
| EP | 1 759 629 | A1 | 3/2007 |
| EP | 3 243 426 | A1 | 3/2020 |
| JP | 2012-187247 | A | 10/2012 |
| WO | 2012146664 | A1 | 11/2012 |
| WO | 2017040692 | A1 | 3/2017 |

OTHER PUBLICATIONS

Dr. Winterfeldt, European Search Report, Jan. 24, 2024, pp. 1-8, European Patent Office, Munich, Germany.

* cited by examiner

ENDOSCOPE HAVING A RIGID OR FLEXIBLE SHAFT TUBE

CROSS-REFERENCE TO RELATED APPLICATIONS

This application claims priority of German Patent Application No. DE 10 2023 123953.8 filed on Sep. 6, 2023, the contents of which are incorporated herein.

TECHNICAL FIELD

The present disclosure relates to an endoscope having a rigid or flexible shaft tube, comprising a rotary drum.

BACKGROUND

Various designs of endoscopes having a rotatable head part are known in principle in the prior art. Endoscopes having a rotary drum are known from DE 10 2020 132 773 B3, DE 10 2020 132 776 A1, DE 10 2020 132 778 A1 of the applicant, in which the rotary drum is rotated in each case by means of a control line which extends on the outside of the shaft in a working channel.

From EP 1 759 629 A1 of the applicant, an endoscope having a rotatable camera holder is known, in which an electric motor drives a gear device which causes the camera holder to rotate. Alternatively, the camera holder can be rotated via a belt arrangement. Rotating the camera holder by means of a belt arrangement is also known from WO 2017/040692 A1.

From EP 3 243 426 A1 of the applicant, an endoscope is known in which the camera can be moved along a rail in order to adjust the field of view.

From US 2015/0359420 A1, an endoscope is known in which the camera holder is mounted on two journals and rotating force is transmitted to the pivotable camera holder via a torque tube.

From D10 2012 206 963 A1, an endoscope having a rotatably mounted camera holder is known, in which the rotation is caused by a drivable roller, which can be operated manually or is controlled by means of a belt drive.

From DE 10 2005 015 522 A1, an intracorporeal probe having a housing in which an image-capturing unit is located is known. The image-capturing unit can be pivoted in the housing in order to change a capturing range of the image-capturing unit by means of this movement. A motor coupled to the image-capturing unit performs the movement.

US 2022/248946 A1 shows an otoscope which comprises a probe and a camera having an image sensor in a housing, which camera is arranged on a probe body of the probe. The camera is mounted so that it can rotate relative to the probe body. The otoscope also comprises cables that allow the camera to rotate.

A disadvantage of the hitherto known prior art is that the known solutions are sometimes highly space-consuming and often consist of many individual components, which makes production and installation challenging and error-prone and difficult to automate.

SUMMARY

The object of the present disclosure is to overcome the disadvantages of the prior art, in particular to propose an endoscope having a rotary drum which can be installed in the distal end of the endoscope in a particularly space-saving and simple manner.

This object is achieved by an endoscope having the features of claim 1.

The following description, description of the figures and the dependent claims relate to advantageous embodiments of the endoscope according to the disclosure.

The features described and claimed in relation to the device shall also be deemed to be correspondingly disclosed and claimable in relation to the method, and vice versa.

As already mentioned above, the endoscope provides a rigid or flexible shaft tube which has a rotary drum and is mounted at a distal end, preferably on a mounting fork, so as to be rotatable about at least one rotational axis.

The definition of distal and proximal is based on the user of the endoscope. Accordingly, distal means the end of the endoscope that is furthest away from the user, i.e., the end that is first inserted into the surgical opening during a surgical procedure. The proximal end is the end closest to the user, for example the end by which the endoscope is held or guided.

The rotary drum comprises a recess in which an associated imaging system is at least partially accommodated, which comprises at least one imaging optical unit and an image sensor, wherein the imaging system is conductively connected to the proximal region of the endoscope by a preferably flexible circuit board.

Furthermore, the endoscope has at least one preferably mechanical control means for moving the rotary drum, in particular for rotating it about the at least one axis of rotation.

According to the disclosure, the rotary drum is designed as a single piece, preferably monolithically, and has at least one preferably resilient control extension.

The present disclosure has recognized that various problems can be solved by the single-piece design of the rotary drum, which thereby achieves overall a compact design that takes up little space in the distal end of the endoscope and can be easily installed.

This is because the single-piece design of the rotary drum makes it possible to mount the rotary drum directly in the mounting fork without any intermediate steps or additionally necessary connecting parts. This facilitates the installation of the rotary drum and also makes it possible, for example, to install the rotary drum on an external mounting fork to test the rotation without integrating it into an endoscope. Since no additional components are required for installation besides the rotary drum, the space required in the distal end of the endoscope for installing the rotary drum is also minimized. Furthermore, the single-piece design makes it possible to transfer, by means of a preferably mechanical control means, a rotational moment directly to the rotary drum to be rotated, without the force having to be passed through connecting elements beforehand, as a result of which a loss of force is avoided while at the same time maintaining a relatively simple design. In addition, the control extension enables a direct or immediate link or connection to the control means, so that the production associated with the transition between the rotary drum and the control means can also be carried out effectively and with little production effort.

The rotary drum preferably consists of a solid and at least partially elastically deformable material that is suitable for extrusion processes, such as stainless steel or titanium. Alternatively, versions made of plastic are also conceivable. This ensures that the control extension can convert the force exerted by a control means into a torque and can deform or bend in the process, at the same time functioning as a resilient return means which causes or at least supports the return of the rotary drum to a defined starting position. The rotary drum can be designed as a permanently installed component, or as an exchangeable component or rotary module. For the exchangeable variant, an additional disposable component version can optionally be provided.

The imaging system consists at least of an imaging optical unit and an image sensor. The imaging optical unit can, for example, be a lens that can preferably be selected and exchanged for the purpose of a particular application. The image sensor can, for example, be in the form of a charged-coupled device (CCD) or complementary metal-oxide-semiconductor (CMOS). Particularly preferably, the image sensor is in the form of a chip-on-the-tip. Other designs of the imaging optical unit and the image sensor are possible.

The flexible circuit board is preferably connected to the image sensor for data transmission and/or energy transmission and preferably connects the distal region to the proximal region of the endoscope. The flexible circuit board is preferably a printed circuit board (PCB) and is made of flexible material, such as polyamide.

The control means of the endoscope preferably consists of a solid material, for example metal, and is in the form of cylindrical wire, for example. This wire design is particularly space-saving; however, a flat control means is also conceivable, it being in the form of a control plate, for example. Preferably, the endoscope comprises at least one control means, but there may also be a plurality of control means that are designed to be of similar type, different or in a combination of similar and different control means.

According to a first advantageous embodiment, the distal end of the endoscope can comprise at least one illumination device which is arranged in such a way that at least the field of view set by the rotary drum and its angle of rotation is illuminated and/or the entire viewing range of the imaging system facilitated by rotation is illuminated.

The illumination device can preferably be connected to the flexible circuit board or have an independent control system and/or power supply. LEDs, for example, can be used for the illumination device. The illumination device can be formed on the shaft tube of the endoscope or on the rotary drum. Furthermore, it is also possible to provide a plurality of illumination devices located both on the shaft and on the rotary drum. The arrangement of the illumination device on the endoscope is advantageous because additional light sources can be dispensed with, particularly in minimally invasive procedures, and the orientation of the illumination to the desired location can be ensured simply and intuitively.

According to a further advantageous embodiment, the control means can be frictionally or integrally connected to the control extension, in particular soldered or welded, as a result of which linear movements of the control means, in particular pushing and pulling the control means along the shaft tube, are translated into a rotational movement of the rotary drum, in particular by means of an elastically deforming deflection of the control extension.

Frictionally connecting the control extension to the control means results in a simple and stable construction for controlling the rotation of the rotary drum. Furthermore, due to the direct transmission of force from the control means to the control extension, relatively little power is required to achieve the rotation, which means that a powerful drive means is not required for the control means and, for example, manual control is also possible. The control extension, which is monolithically connected to the rotary drum and is at least partially elastic, achieves a simple construction with a minimal number of components and parts that are movably mounted on or in relation to one another. According to a further advantageous embodiment, the rotary drum can have at least one, preferably two, journals which are formed preferably monolithically on the rotary drum, via which it is rotatably, preferably exchangeably, mounted on the mounting fork.

The journals are preferably cylindrical, but other designs, such as conical, are also possible. The movable mounting on two journals makes it particularly easy to achieve smooth rotation of the rotary drum. The single-piece design ensures that the journals are held securely in place at the bearing point, this hold being maintained even after a large number of rotations. Furthermore, the journals allow the rotary drum to be easily released from the mounting fork if the rotary drum needs to be exchanged.

According to a further advantageous embodiment, the control extension can be formed on a body of the rotary drum in such a way that an axial angle at center of approximately 90° is formed, which means that the rotary drum can be rotated by 0 to 90° along the rotational axis.

This axial angle at center, which determines the maximum rotation of the rotary drum, can vary by several degrees in the design. An angle of approximately 90° has proven to be particularly advantageous in order to enable the widest possible field of vision with minimal material wear.

According to a further advantageous embodiment, the flexible circuit board can be secured to the image sensor in a curved manner, preferably by 180°. The advantage of this is that the flexible circuit board is unrolled during rotation without being subjected to tension, with the result that the flexible circuit board experiences less material wear. This arrangement also ensures that the flexible circuit board does not get caught on other components during rotation.

According to a further advantageous embodiment, the flexible circuit board can be connected to the image sensor on a side of the rotary drum remote from the shaft tube.

This can also advantageously ensure that the flexible circuit board is unrolled during a rotational movement and experiences less material wear than a flexible circuit board subjected to tension.

According to a further advantageous embodiment, the rotary drum can have a diameter of 2 to 8 mm, preferably 2 to 3 mm.

This means that the rotary drum can be used with common endoscope sizes, for example 4 mm or 10 mm. Furthermore, this size dimension has proven to be particularly advantageous for the processing and production of the rotary drum.

According to a further advantageous embodiment, the control extension can have a material thickness of 30 to 150 μm, preferably 30 to 60 μm and/or a length of 4 to 15 mm, preferably 4 to 6 mm. This material thickness and length have proven to be particularly advantageous for combining the spring-like properties of the control extension with stability, even in the case of frequent rotation.

According to a further advantageous embodiment, the control means can have a diameter of 200 to 1000 μm, preferably 200 to 400 μm.

In this size range, the control means can be designed to be particularly stable and connected to the control extension. Furthermore, this design allows the control means to be guided in the longitudinal direction of the endoscope in such a way as to save space, reliably ensuring the transfer of the control initiated at the proximal end of the endoscope to the control extension.

According to a further advantageous embodiment, the control extension, when the rotary drum is in a relaxed state in which there is no or only an insignificant rotation of the rotary drum, at least partially continues the circular path of the rotary drum and/or is arranged at least partially perpendicular in relation to the axis of rotation of the rotary drum body.

Thus the control extension is provided on the rotary drum in such a way as to save space and can at the same time be easily connected to components arranged in the longitudinal direction of the endoscope, such as the control means. Furthermore, the arrangement of the control extension, which partially continues the circular path of the rotary drum, promotes a fluid rotational movement, thereby reducing material wear on the rotary bearing. According to a further advantageous embodiment, the rotary drum and the control extension can approximate an 'e' shape in the broadest sense when the rotary drum is in the relaxed state.

This further facilitates the particularly space-saving design of the rotary drum. Furthermore, this shape has proven to be particularly robust for the arrangement of the control extension.

According to a further advantageous embodiment, the control extension can be at least partially deformable and, when the rotary drum is in the maximally rotated state, is arranged completely or approximately perpendicularly in relation to the axis of rotation of the rotary drum body.

"Unrolling" the control extension to a position that is approximately perpendicular in relation to the axis of rotation of the rotary drum body results particularly advantageously in the rotary drum being rotated along its circular path. The deformability of the control extension ensures that the rotational movement is particularly fluid, in particular without jerky movements.

According to a further advantageous embodiment, the rotary drum body can have a diameter of 2 to 8 mm, preferably 2 to 3 mm, and is preferably in the shape of a semicircle.

This size of the rotary drum body has proven to be particularly advantageous for the monolithic implementation of the rotary drum for common endoscope sizes, for example 4 mm and 10 mm. The semicircular design of the rotary drum body particularly promotes the robustness of the rotary drum and the stability, especially fluidity, of the rotational movement.

The present disclosure is explained in more detail below with reference to drawings which show merely schematic, exemplary embodiments of the disclosure.

DETAILED DESCRIPTION OF PREFERRED EMBODIMENTS

Figure 1:
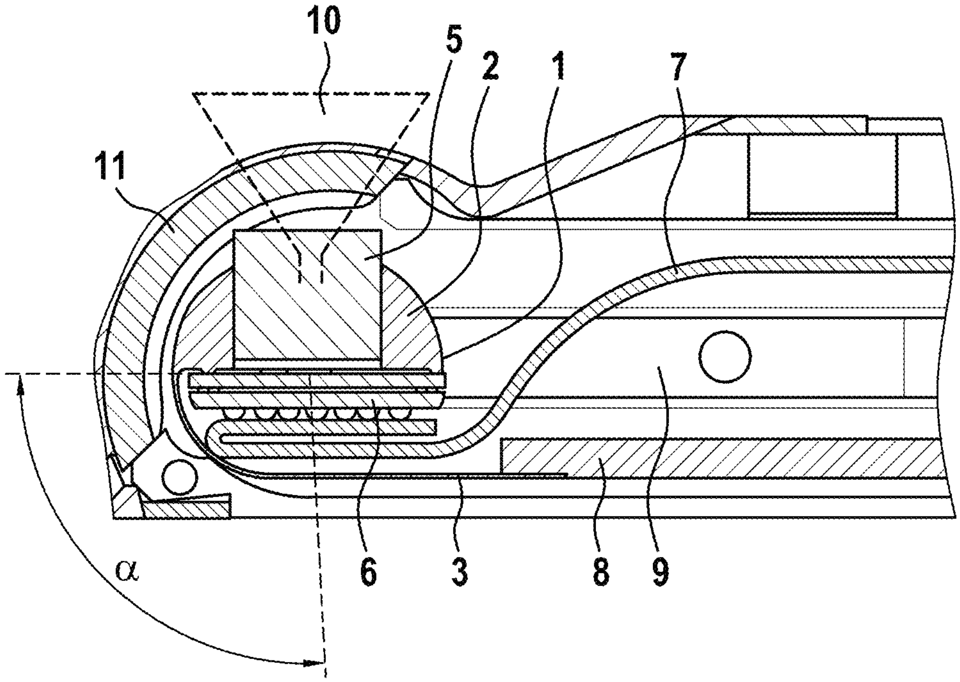
FIG. 1: a schematic cross-sectional representation of a side view of the distal region of an endoscope in a first embodiment

FIG. 1 shows a cross-sectional representation of a side view of an embodiment of the distal region of an endoscope according to the disclosure. With regard to representation and description of a complete endoscope of the type in question, reference can be made, for example, to DE 10 2020 132 778 A1 of the applicant and to FIGS. 1*a* and 1*b* therein, including the associated descriptions of the figures.

The endoscope comprises a mounting fork 9, which is made of metal or plastic, for example. A rotary drum 1 is movably mounted on the mounting fork 9 by means of preferably two journals 4. The journals 4 are formed monolithically on the rotary drum and are preferably cylindrical, although other shapes are also possible. The rotary drum 1 comprises a rotary drum body 2 having a recess in which an imaging optical unit 5, for example a lens, can be received. Furthermore, an image sensor 6 is arranged on the rotary drum body 2, in particular a charged-coupled device (CCD) or complementary metal-oxide-semiconductor (CMOS). A flexible circuit board 7, in particular a printed circuit board (PCB), bent by 180°, is arranged on the image sensor 6. When the rotary drum 1 rotates, the flexible circuit board 7 can unroll and is not subjected to tension, thereby reducing material wear.

The rotary drum 1 further comprises a control extension 3, which is formed monolithically on the rotary drum body 2. The control extension 3 is preferably designed to be resilient and forms an axial angle at center a of 90°, about which the rotary drum 1 can be rotated. A control means 8 is frictionally or integrally connected to the control extension 3, in particular by soldering. The control means 8 extends from the distal to the proximal region of the endoscope and can transmit a signal for rotating the rotary drum 1 from the proximal region to the control extension 3. The control extension 3 is preferably at least partially deformable and, when the rotary drum 1 is maximally rotated, is arranged approximately perpendicularly in relation to the axis of rotation. By rotating the rotary drum 1, the field of view 10 can be rotated by up to 90°.

Figure 2:
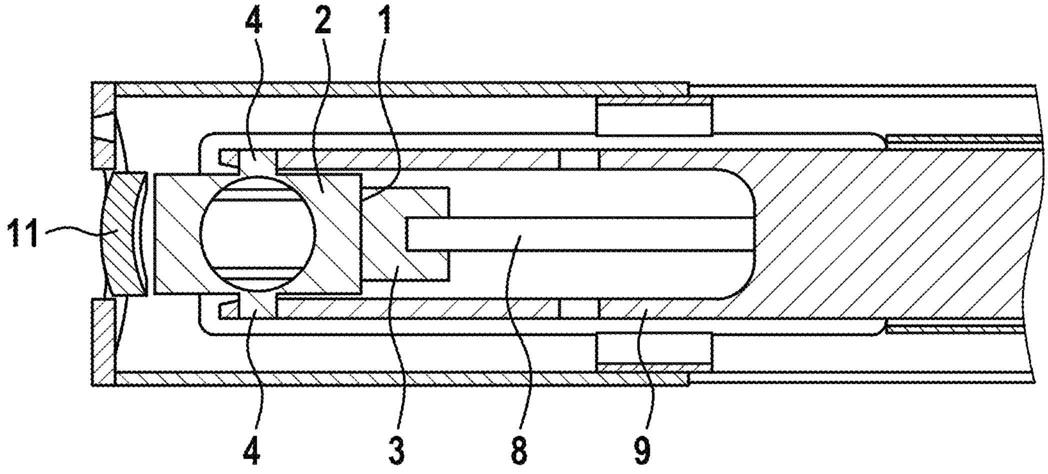
FIG. 2: a schematic cross-sectional representation of a top view of an endoscope in a first embodiment

The endoscope further comprises in its distal region a cover slip 11, which is preferably made of glass or transparent plastic and covers at least the viewing range, preferably a region that extends at least partially beyond the possible field of view. FIG. 2 shows a cross-sectional representation of a top view of an embodiment of the distal region of an endoscope according to the disclosure. Here, too, the endoscope comprises a mounting fork 9, on which a rotary drum 1 is movably mounted via preferably two journals 4. The journals 4 are formed monolithically and preferably cylindrically on the rotary drum 1, although other shapes are also possible. The rotary drum 1 comprises a rotary drum body 2 having a recess. Also monolithically formed on the rotary drum 1 is the control extension 3, to which a control means 8 is frictionally connected, in particular soldered. The control means 8 can direct control of the rotary drum 1 from the proximal to the distal region of the endoscope in order to effect and control a rotation. At the distal end of the endoscope there is also a cover slip 11 which covers at least the viewing range possible by rotation.

Figure 3:
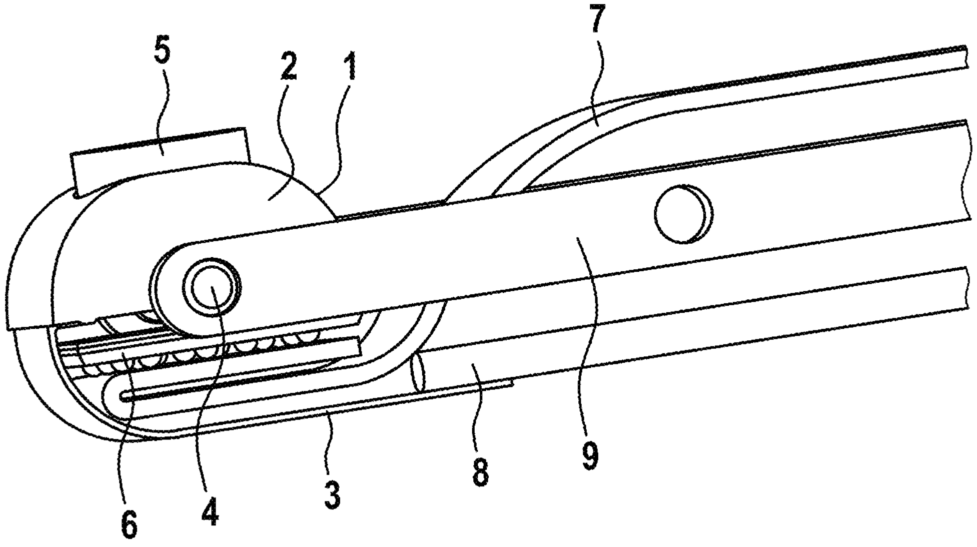
FIG. 3: a perspective side view of the distal region of an endoscope in a first embodiment, without housing

FIG. 3 shows a perspective view of the distal region of an endoscope according to the disclosure without an enclosing housing. The endoscope comprises a mounting fork 9, which is made of metal or plastic, for example. A rotary drum 1 is movably mounted on the mounting fork 9 by means of preferably two journals 4. The journals 4 are formed monolithically on the rotary drum and are preferably cylindrical, although other shapes are also possible. The rotary drum 1 comprises a rotary drum body 2 having a recess in which an imaging optical unit 5, for example a lens, can be received. Furthermore, an image sensor 6 is arranged on the rotary drum body 2. A flexible circuit board 7 bent by 180° is arranged on the image sensor 6 and connects the distal region of the endoscope to the proximal region, in particular for data transmission. When the rotary drum 1 rotates, the flexible circuit board 7 can unroll and is not subjected to tension, thereby reducing material wear. It can be seen particularly well that when the control means 8 is pulled, i.e., when the control means 8 is moved in the proximal direction, the flexible printed circuit board 7 unrolls without colliding with the control means 8 or the control extension 3.

The rotary drum 1 further comprises a control extension 3, which is formed monolithically and preferably resiliently on the rotary drum body 2. A control means 8 is frictionally or integrally connected to the control extension 3, in particular by soldering. The control means 8 extends from the distal to the proximal region of the endoscope and can transmit a signal for rotating the rotary drum 1 from the proximal region to the control extension 3. The control extension 3 is preferably at least partially deformable and, when the rotary drum 1 is maximally rotated, is arranged approximately perpendicularly in relation to the axis of rotation.

Figure 4:
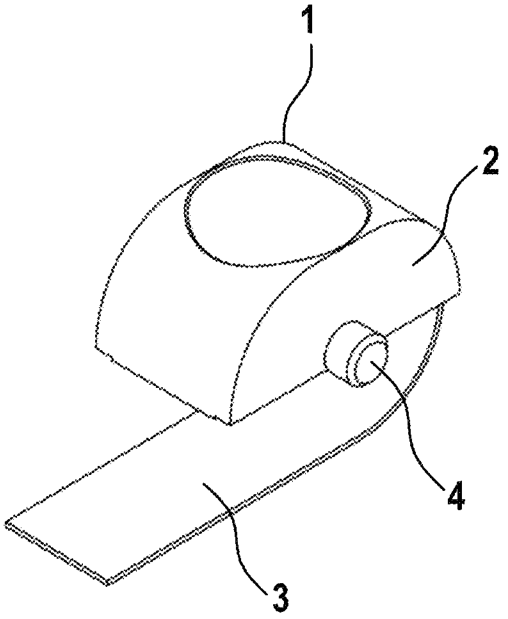
FIG. 4: a perspective view of a rotary drum in a first embodiment

FIG. 4 shows, by way of example, a rotary drum which comprises a rotary drum body on which a preferably resilient control extension 3 is monolithically formed. Journals 4 are also monolithically formed and permit mounting in a mounting fork.

The invention claimed is:

1. An endoscope, comprising:

a rigid or flexible shaft tube; and a rotary drum which is mounted at a distal end so as to be rotatable about at least one rotational axis, wherein the rotary drum includes a recess in which an associated imaging system is at least partially accommodated, which includes at least one imaging optical unit and an image sensor, wherein the imaging system is conductively connected by a circuit board to a proximal region of the endoscope, and wherein the endoscope has at least one control means for moving the rotary drum, wherein the rotary drum is designed as a single piece and has at least one control extension, and wherein the control means is frictionally or integrally connected to the control extension, as a result of which linear movements of the control means—pushing and pulling the control extension along the shaft tube—are translated into a rotational movement of the rotary drum by means of an elastically deforming deflection of the control extension.

2. The endoscope according to claim 1, wherein the distal end of the endoscope comprises at least one illumination device which is arranged in such a way that at least the field of view set by the angle of rotation is illuminated and/or the entire viewing range of the imaging system possible by rotation is illuminated.

3. The endoscope according to claim 1, wherein the rotary drum has at least one journal formed on the rotary drum, via which the rotary drum is rotatably mounted on the mounting fork.

4. The endoscope according to claim 1, wherein the circuit board is in the form of a flexible circuit board.

5. The endoscope according to claim 4, wherein the circuit board is secured to the image sensor in a curved manner.

6. The endoscope according to claim 4, wherein the circuit board is connected to the image sensor on a side of the rotary drum remote from the shaft tube.

7. The endoscope according to claim 1, wherein the rotary drum has a diameter of 2 to 8 mm.

8. The endoscope according to claim 1, wherein at least one control extension has a material thickness of 30 to 150 μm and/or a length of 4 to 15 mm.

9. The endoscope according to claim 1, wherein the control means has a diameter of 200 to 1000 μm.

10. The endoscope according to claim 1, wherein the control extension, when the rotary drum is in a relaxed state, at least partially continues the circular path of the rotary drum and/or is arranged at least partially perpendicular in relation to the axis of rotation of a rotary drum body of the rotary drum.

11. The endoscope according to claim 1, wherein the rotary drum and the control extension together form a generally 'e' shape configuration when the rotary drum is in a relaxed state.

12. The endoscope according to claim 1, wherein a rotary drum body of the rotary drum has a diameter of 2 to 8 mm.

13. An end assembly for an endoscope, the end assembly comprising:

a rotary drum configured to rotate about at least one rotational axis and carrying an imaging system including an imaging optical unit and an image sensor;

a circuit board coupled to the imaging system and extending from the rotary drum;

at least one elongate control member configured to undergo linear displacement;

wherein the rotary drum is a single-piece structure including at least one control extension; and wherein the elongate control member is connected to the control extension such that linear displacement of the elongate control member causes rotation of the rotary drum about the at least one rotational axis via elastic deformation of the control extension.

14. The end assembly of claim 13, wherein the elongate control member is separate from the circuit board and is mechanically coupled to the control extension to transmit mechanical force thereto.

15. The end assembly of claim 13, wherein the circuit board is configured to electrically connect the imaging system and the elongate control member is configured to mechanically actuate the rotary drum.

16. The end assembly of claim 13, wherein the elongate control member comprises a rod.

17. The end assembly of claim 13, wherein the elongate control member comprises a wire.

18. The end assembly of claim 13, wherein the control extension, in a relaxed state of the rotary drum, extends along at least a portion of a circular path of the rotary drum body and is oriented at least partially transverse to the axis of rotation of the rotary drum body.

19. The end assembly of claim 13, wherein the rotary drum and the control extension together define a generally curved configuration.

20. The end assembly of claim 13, wherein the rotary drum and the control extension, in a relaxed state of the rotary drum, together define a generally 'e'-shaped configuration.

* * * * *